United States Patent
Michler et al.

(10) Patent No.: US 9,603,590 B2
(45) Date of Patent: Mar. 28, 2017

(54) SINGLE-ARM STABILIZER HAVING SUCTION CAPABILITY

(71) Applicants: Robert E. Michler, Riverside, CT (US); Albert N. Santilli, Pepper Pike, OH (US)

(72) Inventors: Robert E. Michler, Riverside, CT (US); Albert N. Santilli, Pepper Pike, OH (US)

( * ) Notice: Subject to any disclaimer, the term of this patent is extended or adjusted under 35 U.S.C. 154(b) by 24 days.

(21) Appl. No.: 14/216,289

(22) Filed: Mar. 17, 2014

(65) Prior Publication Data

US 2014/0303446 A1    Oct. 9, 2014

Related U.S. Application Data

(60) Provisional application No. 61/801,498, filed on Mar. 15, 2013.

(51) Int. Cl.
| | | |
|---|---|---|
| *A61B 1/32* | (2006.01) | |
| *A61B 17/02* | (2006.01) | |
| *A61B 17/30* | (2006.01) | |

(52) U.S. Cl.
CPC ......... *A61B 17/0206* (2013.01); *A61B 17/02* (2013.01); *A61B 2017/0243* (2013.01); *A61B 2017/306* (2013.01)

(58) Field of Classification Search
CPC .............. A61B 17/02; A61B 2017/306; A61B 2017/0243; A61B 17/3431; A61B 17/0206
USPC ................................. 600/201–210
See application file for complete search history.

(56) References Cited

U.S. PATENT DOCUMENTS

| | | | |
|---|---|---|---|
| 5,891,017 A | 4/1999 | Swindle et al. | |
| 5,967,972 A | 10/1999 | Santilli et al. | |
| 5,984,864 A * | 11/1999 | Fox ........................ | F16M 11/14 600/201 |
| 6,361,492 B1 | 3/2002 | Santilli | |
| 6,383,134 B1 | 5/2002 | Santilli | |
| 7,438,680 B2 | 10/2008 | Guenst et al. | |
| 7,497,824 B2 | 3/2009 | Taylor | |
| 7,503,891 B2 | 3/2009 | Green, II et al. | |
| 2007/0042016 A1* | 2/2007 | Nayak ................ | A61B 17/3478 424/423 |
| 2007/0088203 A1* | 4/2007 | Lau ..................... | A61B 17/0218 600/205 |
| 2007/0232865 A1* | 10/2007 | Efinger ................. | A61B 17/02 600/227 |
| 2009/0030270 A1* | 1/2009 | Arai ....................... | A61B 17/02 600/37 |

* cited by examiner

*Primary Examiner* — Mary Hoffman
*Assistant Examiner* — Tara R Carter
(74) *Attorney, Agent, or Firm* — Wayne D. Porter, Jr.

(57) ABSTRACT

A single-arm stabilizer having suction capability includes a single, small leg through which suction can be applied. The leg has an upper surface and a lower surface that are spaced apart to define a chamber. The lower surface includes a plurality of openings that are disposed adjacent each other. A support arm is connected to the leg in order to position the leg as desired. A suction line is in fluid communication with the chamber in order to create a vacuum within the chamber. The stabilizer can be used to stabilize any desired portion of a patient's body, but is particularly effective at stabilizing the septum of a patient's heart. Such stabilization can be accomplished by inserting the leg into the patient's heart through the aorta.

6 Claims, 1 Drawing Sheet

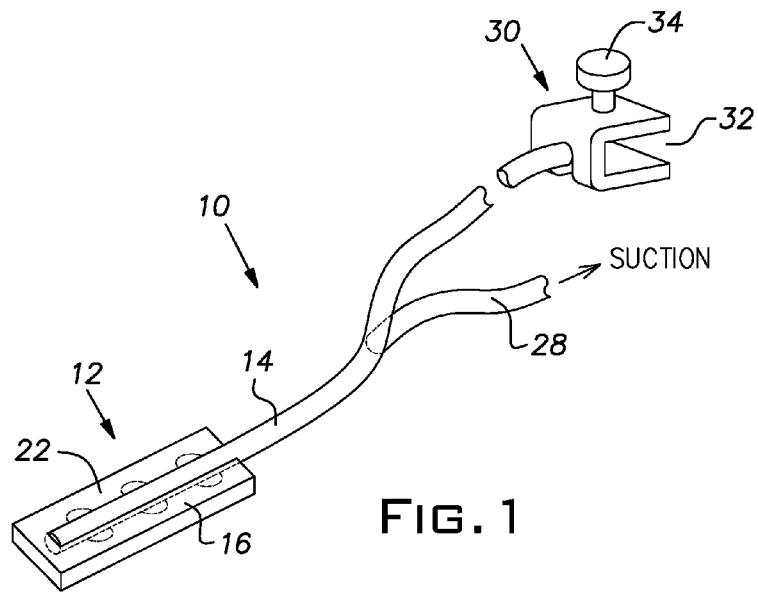
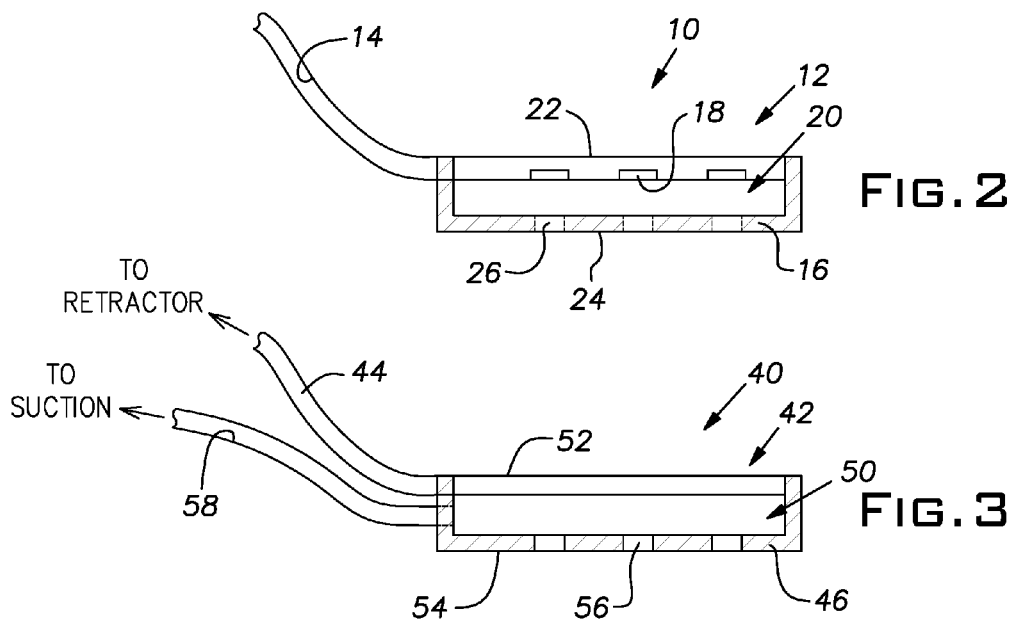

SINGLE-ARM STABILIZER HAVING SUCTION CAPABILITY

REFERENCE TO PROVISIONAL APPLICATION

The present application claims priority to U.S. provisional application Ser. No. 61/801,498, entitled Single-Arm Stabilizer Having Suction Capability, filed Mar. 15, 2013 by Robert E. Michler and Albert N. Santilli, the disclosure of which is incorporated herein by reference in its entirety.

REFERENCE TO RELATED PATENTS

The present application refers to and incorporates by reference the entirety of U.S. Pat. Nos. 6,383,134, 6,361,492, and 5,967,972.

BACKGROUND OF THE INVENTION

Field of the Invention

The invention relates to surgical stabilizers of the type used in cardiac surgery and, more particularly, to a single-arm surgical stabilizer having suction capability.

Description of the Prior Art

Idiopathic hypertrophic subaortic stenosis (IHSS), also known as hypertrophic cardiomyopathy, is a disease characterized by marked hypertrophy of the left ventricle, involving in particular the interventricular septum and the left ventricular outflow tract. During systole, the hypertrophied muscle in the outflow tract often narrows this region sufficiently to produce obstruction to left ventricular ejection. In hypertrophic cardiomyopathy, the enlargement and arrangement of muscle fibers are abnormal, leading to thickened heart walls. The most thickening tends to happen in the left ventricle (the heart's central pumping chamber), especially in the septum, the wall that separates the left and right ventricles. The thickening reduces the size of the pumping chamber and obstructs blood flow. It also prevents the heart from properly relaxing between beats and so filling with blood. Types of Hypertrophic cardiomyopathy includes ASH and HOCM.

There are a number of treatment options for IHSS, including lifestyle changes, medications, pacemakers and surgery. Various drugs are used to treat this disease. They comprise beta blockers, calcium channel blockers, antiarrhythmic medications, and diuretics.

Pacemakers vary the pattern and reduce the force of the heart's contractions. The pacemaker can diminish the degree of obstruction and so relieve symptoms. Surgery generally calls for removal of part of the thickened septum (the muscle wall separating the chambers) that is blocking the blood stream. Surgery to eliminate the thickening eases symptoms in about 70 percent of patients but results in death in about 1 to 3 percent of patients. Also, about 5 percent of those who have surgery develop a slow heartbeat, which is then corrected with a pacemaker.

In the course of surgically treating cardiac problems such as IHSS or HOCM it is necessary to position the septum in a desired position. This can be problematic because it is difficult to grasp septum, particularly if the septum is accessed through the aorta.

Desirably, a technique would be available that would permit the surgeon to be able to grasp the septum during the course of conducting a surgical procedure so as to stabilize the septum. Preferably, such a technique would be able to push or pull the septum to any desired position and hold it there as long as necessary.

SUMMARY OF THE INVENTION

In response to the foregoing concerns, the present invention provides a new and improved surgical retractor that is able to engage or grasp tissue, particularly the septum. The retractor according to the invention can be used in various types of surgical procedures, although it is especially effective in cardiac surgery involving the septum. In a preferred embodiment, the stabilizer includes a single, small leg through which suction can be applied through the lower surfaces thereof. The suction enables the surface of the septum or other surface to be grasped by the stabilizer, thereby preventing the septum from moving. The stabilizer is small enough that it can be inserted through the aorta.

The leg has an upper surface and a lower surface that are spaced apart to define a chamber, the lower surface including a plurality of openings which are disposed adjacent each other. When a suction tube is in fluid communication with the chamber, a vacuum can be applied to the openings in the leg so as to attract the septum to the leg. In the preferred embodiment, a plastic housing forms that portion of the leg in contact with the septum.

The stabilizer also includes a support arm each having a first end and a second end, the first end of the support arm being connected to the leg and the second end of the support arm being connected to a supporting member such as a cardiovascular retractor. Preferably the support arm is made of a malleable material so that it can be bent into a desired position during the course of a surgical procedure while being strong enough to hold the septum in a desired position. Suction can be applied through the support arm if it is hollow or through a separate suction line connected to the chamber.

The foregoing features and advantages will be apparent from the accompanying drawings and description that follow.

BRIEF DESCRIPTION OF THE DRAWINGS

FIG. 1 is a perspective view of a surgical retractor according to the invention in which a suction capability is provided;

FIG. 2 is a cross-sectional view of the retractor of FIG. 1; and

FIG. 3 is a cross-sectional view of an alternate embodiment of the surgical retractor according to the invention.

DESCRIPTION OF THE PREFERRED EMBODIMENT

Referring to FIGS. 1 and 2, a surgical stabilizer according to the invention is indicated generally by the reference numeral 10. The stabilizer 10 includes a hollow leg 12. The leg 12 is formed by an elongate, hollow arm 14 to which a housing 16, preferably of a plastic material, is attached. The end of the leg 12 is provided with a plurality of spaced openings 18. The housing 16 is hollow and defines a chamber 20. The housing 16 and the arm 14 form an upper surface 22. The underside of the housing 16 forms a lower surface 24. The lower surface 24 has a plurality of openings 26 that are disposed adjacent to each other, in this instance in a straight line.

A suction line 28 is spliced into the hollow arm 14 at a location remote from the housing 16. The suction line 28 can be connected to a wall-mounted suction port typically found in operating rooms. A clamp 30 is mounted at the distal end of the arm 14. The clamp has a C-shaped opening 32 that can be fitted about a generally flat portion of a cardiovascular retractor and retained in place there by a thumbscrew 34.

Referring to FIG. 3, an alternative embodiment of the invention is indicated by the reference numeral 40. The embodiment 40 is similar to the embodiment 10. The stabilizer 40 includes a hollow leg 42. The leg 42 is formed by an elongate, solid arm 44 to which a housing 46, preferably of a plastic material, is attached. The housing 46 is hollow and defines a chamber 50. The housing 46 and the arm 44 form an upper surface 52. The underside of the housing 46 forms a lower surface 54. The lower surface 54 has a plurality of openings 56 that are disposed adjacent to each other, in this instance in a straight line.

A suction line 58 is connected to the housing 46 and is in fluid communication with the chamber 50. The suction line 58 can be connected to a wall-mounted suction port typically found in operating rooms. A clamp (not shown) similar or identical to the clamp 30 can be used to connect the arm 44 to a stable member such as a retractor.

Since the stabilizers 10, 40 are expected to be inserted through the aorta, they must be very small. Typically, the legs 12, 42 will be about 2 or 3 cm long, 5 to 7 mm wide, and approximately 4 or 5 mm high. The arms 14, 44 will be about 6 cm long.

As will be appreciated from the foregoing description, the stabilizer according to the invention can apply suction to the lower surfaces 24, 54 of the legs 12, 42 in an effective manner. The stabilizer according to the invention enables the septum or other engaged surface to be pushed or pulled into a desired position for the course of the surgical procedure.

Although the invention has been described in its preferred form with a certain degree of particularity, it will be understood that the present disclosure of the preferred embodiment has been made only by way of example and that various changes may be resorted to without departing from the true spirit and scope of the invention as disclosed and claimed.

What is claimed is:

1. A method of stabilizing the septum of a patient's heart, comprising the steps of:
   providing a single-arm stabilizer having:
      a single, small leg through which suction can be applied through the lower surfaces thereof, the leg having an upper surface and a lower surface that are spaced apart to define a chamber, the lower surface including a plurality of openings that are disposed adjacent each other;
      a support arm having a first end and a second end, the first end of the support arm being connected to the leg and the second end of the support arm being connectable to a supporting member such as a cardiovascular retractor; and
      a suction line having a first end and a second end, the first end of the suction line being in fluid communication with the chamber and the second end being connectable to a suction source, whereby, when the second end is connected to a suction source a vacuum will be established within the chamber;
   disposing the leg in contact with the septum of the patient's heart by inserting the leg through the patient's aorta; and
   applying a vacuum to the chamber so that the lower surface of the leg is connected to the septum of the patient's heart.

2. The method of claim 1, wherein the step of providing a single-arm stabilizer includes (a) providing a single, small leg in the form of an elongate, generally rectangular housing and (b) providing a support arm in which the first end of the support arm extends through the housing and defines a portion of the upper surface of the leg.

3. The method of claim 1, wherein the step of applying a vacuum to the chamber so that the lower surface of the leg is connected to the desired portion of the patient's body is accomplished by providing a support arm in which the first end of the support arm is hollow and includes a terminal portion having one or more openings in fluid communication with the chamber, and the first end of the suction line is connected to the support arm adjacent the first end thereof such that the suction line can apply a vacuum to the chamber through the first end of the support arm.

4. The method of claim 1, wherein the step of applying a vacuum to the chamber so that the lower surface of the leg is connected to the desired portion of the patient's body is accomplished by connecting the first end of the suction line directly to the leg.

5. The method of claim 1, wherein the step of providing a single-arm stabilizer includes providing a housing made of a plastics material.

6. The method of claim 1, wherein the step of providing a single-arm stabilizer includes providing a leg about 2-3 cm long, 5-7 mm wide and about 4-5 mm high.

* * * * *